United States Patent [19]

Bore et al.

[11] 4,224,950
[45] Sep. 30, 1980

[54] APPARATUS FOR MEASURING THE AMOUNT OF SEBUM SECRETED BY THE SKIN OF A LIVING SUBJECT

[75] Inventors: Pierre Boré, Montfermeil; Lucienne Tourenq, Livry-Gargan, both of France

[73] Assignee: L'Oreal, Paris, France

[21] Appl. No.: 42,551

[22] Filed: May 25, 1979

[30] Foreign Application Priority Data

May 31, 1978 [FR] France ............... 78 16231

[51] Int. Cl.³ .................. A61B 5/00; A61B 10/00
[52] U.S. Cl. .................................. 128/759; 356/36; 356/70
[58] Field of Search ............ 128/749, 759, 630, 633, 128/634, 743; 356/36, 70

[56] References Cited

U.S. PATENT DOCUMENTS

| 2,224,123 | 12/1940 | Wilson | 356/70 |
| 2,291,562 | 7/1942 | Reysa et al. | 356/70 |
| 3,906,933 | 9/1975 | Tur et al. | 128/759 |

Primary Examiner—Kyle L. Howell
Attorney, Agent, or Firm—Brisebois & Kruger

[57] ABSTRACT

Apparatus for measuring the secretions of sebum of a skin sample of a living subject comprises a frosted glass plate spring urged to project from a casing (using a calibrated spring). When pressed against the forehead of a living subject the frosted plate retracts yieldably to collect sebum under reproducible conditions.

A reference scale inside the casing of the apparatus is illuminated from a known light source and is observed from outside by looking through the greasy plate. The sebum secretion is measured by changing the position of the scale, or changing the line thickness of a reference mark on the scale until a sharp, fine image of the reference mark can be seen.

11 Claims, 7 Drawing Figures

APPARATUS FOR MEASURING THE AMOUNT OF SEBUM SECRETED BY THE SKIN OF A LIVING SUBJECT

In cosmetics, dermatology, and the pharmaceutical field, different types of apparatus exist for measuring the amount of sebum secreted by the skin of a living subject whom it is desired to study. Most of these apparatuses are based on the fact that, when sebum is deposited on a translucent element, such as a frosted glass plate, the element becomes increasingly transparent, the greater the amount of sebum applied. The method of measurement consists in subjecting the translucent element, covered with sebum, to a luminous flux and in measuring, by means of a photoelectric receiver, the amount of light which passes through the translucent element by virtue of transparency.

Nevertheless, the apparatuses of the type indicated above are intended for use by qualified technicians in laboratories and not for use by those who are not skilled in laboratory techniques. In fact, it is necessary to sample the sebum in accordance with a method of operation which is predetermined, in particular as regards the pressure of application of the translucent element on the zone of skin to be studied, and as regards the contact time. In order to facilitate the sampling operations, a so-called "sebumeter" apparatus has already been proposed in German Offenlegungsschrift No. 2,353,224, which apparatus is produced in two separate parts, namely a sampling device and an actual measuring device which is equipped with a photoelectric receiver and a source of illumination. The sampling device comprises a casing, from which projects a sample-holder on which the translucent element is arranged. The sample-holder is connected to the casing by a calibrated spring so as to enable the sample-holder to be applied under an approximately constant pressure to the zone of skin to be studied. After having sampled the sebum, the sample holder is carried into the photoelectric measuring device of the apparatus in order to evaluate the amount of sebum secreted.

It is an object of the present invention to produce a compact measuring apparatus which combines, in one and the same casing, both the sampling device and the device for reading the variation in the transparency of the translucent element. The apparatus according to the invention is also to be easy to use and should require little or no additional equipment. Thus, this apparatus is intended for use outside the laboratory, in premises which are not specially equipped, such as hair salons, where the apparatus can be made available to any person who wishes to determine, by a simple and rapid method, the greater or lesser state of greasiness of a zone of skin. In particular, it is known that there is a close correlation between the state of greasiness of the skin on the forehead near the scalp and the activity of the sebaceous glands, with the result that the apparatus according to the invention may make it possible to measure the greater or lesser activity of the sebaceous glands. Furthermore, whereas the so-called sebumeters of the prior art are provided with a relatively expensive photoelectric receiver, the apparatus according to the invention comprises a simple illuminated rule which makes it possible to measure the transparency of the translucent element to which the sebum is applied.

Accordingly the present invention provides apparatus for measuring the amount of sebum secreted by the skin of a living subject, said apparatus comprising a casing; a sample-holder projecting from said casing and capable of sliding relative to the casing and of becoming flush integral with the casing upon yielding of at least one calibrated spring; a translucent element carried by said sample-holder and intended to be applied to the zone of skin to be studied; a scale within said casing and carrying at least one reference mark or graduation capable of being positioned inside the casing opposite said translucent element; and a light source within the casing and arranged to emit a luminous flux in the direction of said scale; whereby the amount of sebum deposited on the sample-holder can be read by observation of said reference mark or graduation through the translucent element.

The invention envisages several reading methods based on the use of a scale. In a first variant, the scale is mounted on a movable support which is moved relative to the translucent element to adjust the sharpness of the reference mark or pattern carried by the scale; the movement of the support is measured by means of a graduated scale which defines several zones, each of which corresponds to an amount of sebum which is determined by calibrating the apparatus using a conventional method of photometric or chemical determination. The support can also be fixed relative to the translucent element, in which case the illumination of the scale is varied, for example by means of a variable resistance system equipped with a voltmeter which makes it possible to read directly the amounts of sebum measured. The scale itself may carry a series of reference marks and can be moved in a plane parallel to the plane of the translucent element in order to find the reference mark which, by virtue of transparency, appears to be sharpest and thus this mark corresponds to the amount of sebum sampled. For this latter case, several kinds of scale can be envisaged: the first consists of a plate which is slid through the casing; the second consists of a circular disc which is caused to pivot relative to the casing of the apparatus so as to bring the reference marks, located on the rule, successively opposite the translucent element; and the third requires the scale to be a rotor which is housed inside the casing and whose wall has a series of reference marks which, by rotating the drum about an axis parallel to the translucent element, can be successively presented at right angles to the translucent element.

In a preferred embodiment of the apparatus, the light source consists of at least one illuminating lamp placed between the scale and the translucent element; the illuminating lamp is energisable by a self-contained source of electrical energy, such as an electric battery, placed inside the casing; the translucent element is a frosted glass plate.

In a first modified embodiment the scale is fixed to a support which can move translationally inside the casing, relative to the translucent element, the movement of the support being measured by means of graduations provided on the outer wall of the casing; the support is a cylinder which houses the self-contained source of electrical energy and which carries the illuminating lamp or lamps, the end of the cylinder which is located opposite the translucent element being closed by the scale; the support comprises, on the outside, a slider which travels along a rectilinear slot provided in the wall of the casing, parallel to the sliding axis of the support, the said graduations being located on one of the parallel edges of the said slot; the abovementioned slider cooperates with a milled nut which makes it possible to hold the scale against translational movement relative to the box.

In a second modified embodiment, the scale carries several reference marks and is intended to be moved in a plane parallel to the mean plane of the translucent element so as to bring each of the reference marks on the scale successively opposite the translucent element. In a first case, the scale is in the form of a small plate which can be introduced into the casing by virtue of two apertures made in the wall of the said casing, these apertures guiding the small plate for translational movement in a plane parallel to the plane of the translucent element. In a second case, the scale is in the form of a circular disc which is mounted so as to pivot in a plane parallel to the plane of the translucent element, at least a sector of the disc penetrating inside the casing through a suitable slot to come opposite the translucent element.

In a third modified embodiment, the scale is in the form of a rotor which is mounted so as to pivot inside the casing about an axis approximately parallel to the plane of the translucent element, the side wall of the rotor carrying a series of reference marks which, by rotation of the rotor, can be successively presented at right angles to the translucent element; the side wall of the rotor delimits a regular prism, the base of which is preferably a square, the axis of the prism coinciding with the axis of rotation of the rotor, each side face of the prism carrying a reference mark; the rotation of the rotor is controlled by any suitable device such as, for example, a milled knob.

Three embodiments of the invention, which are shown in the attached drawing, will be described below, by way of purely illustrative and non-limiting examples, in order to provide a better understanding of the subject of the invention. In this drawing:

DETAILED DESCRIPTION OF PREFERRED EMBODIMENTS

Figure 1:
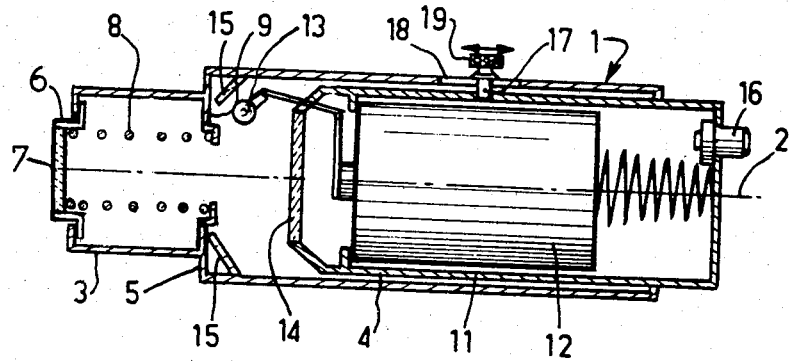
FIG. 1 schematically represents, in axial section, a "sebumeter" apparatus according to a first embodiment of the invention.
Figure 2:
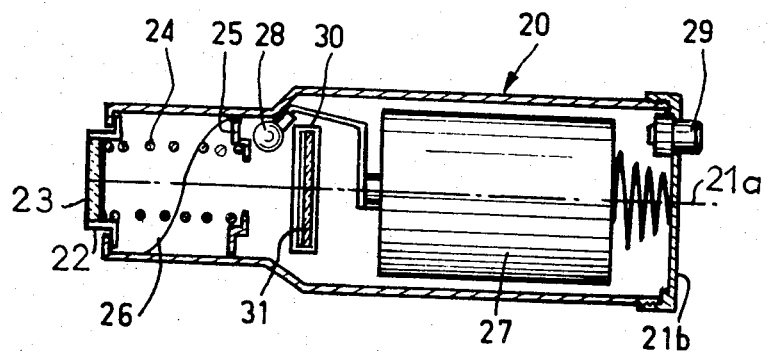
FIG. 2 sechmatically represents, in axial section, a "sebumeter" apparatus according to a second embodiment of the invention.
Figure 3:
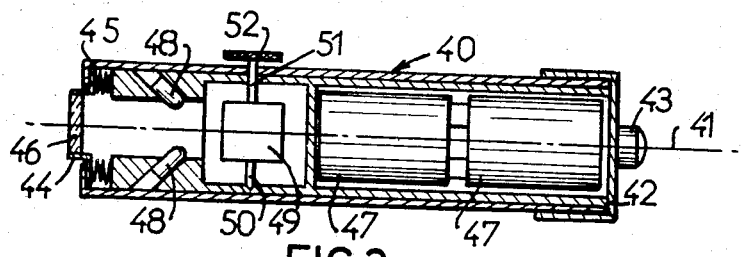
FIG. 3 schematically represents, in axial section, a "sebumeter" apparatus according to a third embodiment of the invention.
Figure 1A:
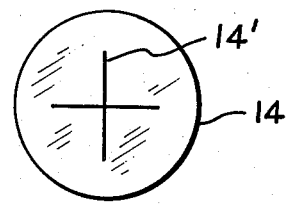
FIG. 1A is a front view of the scale of FIG. 1, showing its reference pattern or target.
Figure 1B:
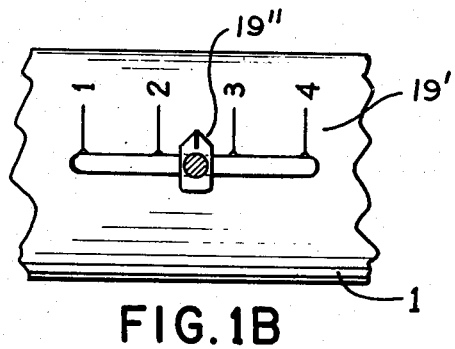
FIG. 1B is a partial enlarged top plan view of the "sebumeter" of FIG. 1, showing the indicia on the housing and its slidable pointer.

The apparatuses in FIGS. 1 to 3 are more particularly designed for evaluating the activity of the sebaceous glands. In fact it is known that, for any individual, a close correlation exists between the amount of sebum secreted by the skin on the forehead near the scalp and the greater or lesser activity of sebaceous glands.

The "sebumeter" apparatus in FIG. 1 comprises a box 1, of generally cylindrical shape, which is open at both its ends. The axis of the casing 1 has been denoted by 2. The casing 1 comprises two parts 3 and 4, of different diameters, which are joined together by an annular shoulder 5.

In the smaller diameter part 3 of the casing 1, a sample-holder 6 is mounted so as to slide along the axis 2 of the casing. When the sample-holder is not subjected to any compression, it normally projects outside the casing 1. The sample-holder 6 is in the form of a cylindrical sleeve, the axis of symmetry of which approximately coincides with the longitudinal axis of the cylindrical casing and which is closed at its outer end by a frosted glass plate 7. The frosted glass plate 7 is arranged perpendicular to the axis of sliding of the sample-holder 6, which coincides with the axis 2 of the casing. The frosted glass plate 7 is detachably fixed to the sample-holder 6 by any suitable means, for example using a slide provided at the end of the sample-holder 6. Thus, the frosted glass plate 7 can be changed before each measurement step which consists of applying the said plate to the forehead of the person for whom it is desired to evaluate the activity of the sebaceous glands.

A suitably calibrated compression spring 8 is fixed at one of its ends to the sample-holder 6 and at its other end to a ring 9 integral with the casing 1 and in this case coplanar with the shoulder 15. In this embodiment, the force required to push the sample-holder 6 into the casing 1 is selected to be about 1 kg.

In the larger diameter part 4 of the casing is a scale support 11 which can slide along an axis coincident with the longitudinal axis 2 of the casing. The scale support 11 is in the form of a cylinder closed at both its ends, inside which is housed an electric battery 12 for energising an illuminating lamp 13. The end of the scale support 11 which is located opposite the frosted glass plate 7 is closed by a scale 14 on which a suitable reference mark 14' is engraved. The scale 14 is illuminated by the lamp 13 carried by the support 11, and the emitted luminous flux is reflected by two mirrors 15 towards the scale 14. The lamp 13 is intended to emit a sufficient flux of yellow, white or green light to enable a user with average eyesight to read the scale easily. The scale 14 is approximately parallel to the frosted glass plate 7. The end of the support 11 which is opposite to that where the rule 14 is arranged is closed by a circular wall provided with an electric switch 16 of a conventional type, which makes it possible to switch the lamp 13 on or off.

The support 11 is integral with a slider 17 which travels along a rectilinear slot 18 located parallel to the sliding axis of the support 11. The slider 17 can cooperate with a milled nut 19 which makes it possible to lock the translational movement of the support 11 inside the box. Graduations 19' are arranged along one of the parallel edges of the slot 18 dividing that edge into four zones of four different states of greasiness, to be indicated by pointer 19''.

The "sebumeter" apparatus which has now been described is used as follows: firstly the apparatus is pressed for about 10 seconds against the forehead of the person, preferably at the central part of the forehead, keeping the sample-holder 6 pushed inside the smaller diameter part 3 of the casing 1 so that the application is carried out under an approximately constant pressure. The sebum which is removed onto the frosted glass plate 7 has the effect of increasing the translucency of the plate 7 as a function of the amount of sebum deposited. The translucency of the frosted glass 7 is read by initially operating the switch 16 in order to illuminate the scale 14, and then moving the support 11 until the pattern 14' on the scale 14 appears visible and sharply defined, by virtue of transparency. It is then sufficient to record the zone of the graduated scale opposite which the slider 17 is located in order to characterise the activity of the sebaceous glands by a numerical datum. It is found that a close correlation exists between the values given by the apparatus in FIG. 1 and those which are given by laboratory analyses.

According to a variant of the device in FIG. 1, it is also possible to arrange for the scale support to be fixed and to vary the illumination of the scale, for example, by varying the supply voltage of the illuminating lamp 13 by any known means, the translucency in this case being read by means of a voltmeter which enables the measured state of greasiness to be displayed.

FIG. 2 of the attached drawing shows yet another embodiment of a "sebumeter" apparatus according to the invention. This apparatus comprises a cylindrical casing 20 having an axis of revolution 21a. The casing 20 is closed at one of its ends by a circular wall 21b and open at its other end so as to allow the passage of a sample-holder 22 which is capable of sliding along an axis essentially coincident with the axis 21a of the casing. The sample-holder 22 is in the form of a cylindrical sleeve having releasably fixed to one of its ends a frosted glass plate 23, used for sampling the sebum. The frosted glass plate 23 extends perpendicular to the sliding axis of the sample-holder 22. A calibrated spring 24 connects the sample-holder 22 to a movable adjusting ring 25 which can be moved closer to, or further away from, the open end of the casing 20 by virtue of a helical cam slot 26. The position of the movable ring 25 is adjusted so as to cause the sample-holder 22 to be pushed completely inside the casing 20 when a force of about 1 kg is exerted on the sample-holder.

Inside, near its end wall 21b, the casing 20 comprises an electric battery 27 which is used for supplying an illuminating lamp 28. A switch 29, provided on the end wall 21b, makes it possible to switch off and on a lamp 28 energised by the battery 27.

Figure 2A:
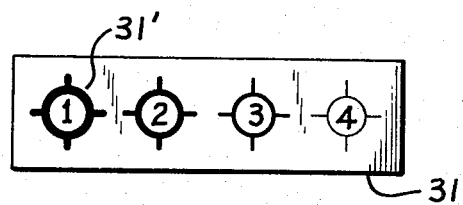
FIG. 2A is a front view of the slidable scale used with the "sebumeter" of FIG. 2, and shows the different line thicknesses of reference marks on the scale.

Two diametrically opposite apertures 30 are made in the wall of the casing 20. They are located perpendicular to the axis 21a of the casing and parallel to the frosted glass plate 23 and are intended to guide a longitudinally movable scale 31. The scale 31 is in the form of a plate comprising a series of four reference marks 31' which together define four different states of greasiness. These four reference marks 31' can consist of any patterns of which the line thickness, for example, varies gradually from one reference mark to another, as shown at FIG. 2A.

In order to use the "sebumeter" apparatus which has now been described, it is necessary to press the frosted glass plate 23 for about ten seconds to the central part of the forehead of a person for whom it is desired to know the activity of the sebaceous glands, this application being carried out under a pressure which is such that the sample-holder 22 is pushed inside the casing 20. Once this sampling operation has been completed, the lamp 28 is illuminated by operating the switch 29, and the scale 31 is then slide across through the two guide apertures 30 so as to bring the four reference marks 31' (FIG. 2A) on the scale successively opposite the frosted glass plate 23. The higher or lower translucency of the frosted glass plate 23 is read by assessing which reference mark on the scale appears to be the sharpest.

Figure 2B:
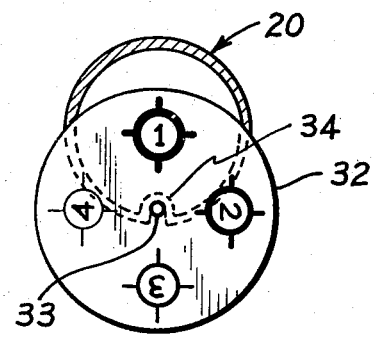
FIG. 2B is a front view of a rotatable disc scale usable with a modified version of the "sebumeter" of FIG. 2, and which is mounted to rotate on an axis at the side wall of the "sebumeter" casing.

Instead of slidable scale 31, a scale can be used in the form of a circular disc 32 (FIG. 2B), which can rotate in a plane parallel to that of the frosted glass 23 about an axle 33 which can be snapped into U-shaped bearing clips 34 on the sidewall so as to be able to bring the four reference marks 35 successively opposite the frosted glass. The slot in the housing to receive disc 32 extends about 180° circumferentially, and can open downwardly.

FIG. 3 of the drawing shows a third variant of the "sebumeter" apparatus according to the invention. This apparatus comprises a cylindrical casing 40 having an axis of revolution 41. The casing is closed at one of its ends by a cap 42 carrying a switch 43. Inside the other open end of the casing 40 is a sample-holder 44 which is subjected to the action of a calibrated spring 45 for a sliding movement along the axis 41. A frosted glass plate 46, used for sampling the sebum, is releasably fixed to the sample-holder 44. The frosted glass plate 46 extends perpendicular to the sliding axis of the sample-holder 44. Two electric batteries 47, which supply four diametrically opposite illuminating lamps 48, are arranged inside a compartment located near the cap 42, the switch 43 being used to illuminate and extinguish these four lamps.

The essential characteristic of the sebumeter apparatus in FIG. 3 lies in the configuration of the scale. The latter is in the form of a rotatable cube 49, one of the axes of which is parallel to the plane of the frosted glass plate 46. This cube is carried by two pivots 50 and 51 which are joined to the two opposite transverse faces of the cube. The two pivots 50 and 51 are located along that axis of the cube which is parallel to the frosted glass plate 46. The pivot 51 extends outside the casing by means of a milled knob 52 which is used to rotate the cube. Four reference marks, defining four different states of greasiness, are made on the side faces of the rotatable cube 49. These four reference marks can advantageously consist of the numerals 1 to 4 and patterns of differing line thickness, only numeral 3 and its pattern being shown.

The sebumeter apparatus in FIG. 3 is used as follows: a frosted glass plate 46 is mounted on the sample-holder 44 and then applied for about ten seconds to the forehead of the person for whom it is desired to know the activity of the sebaceous glands. This step is carried out with a pressure of application which is sufficient to cause the projecting part of the sample-holder 44 to be pushed inside the casing 40. Once the sample has been taken, switching on the four lamps 48 in front of the cube causes them to illuminate the cube with a sufficient flux of light to enable the scale to be easily read. By operating the milled knob 52, the user rotates the cube-shaped scale so as to present successively the four side faces, on which the reference numbers 1 to 4 are located, opposite the frosted glass plate 46. The higher or lower translucency of the frosted glass plate 46, onto which the sebum has been removed, is read by assessing which of the numerals 1, 2, 3 or 4 on the scale appears to be the sharpest.

Of course, the embodiments described above in no way imply a limitation and will be able to form the subject of any desirable modification without thereby going outside the scope of the invention.

We claim:

1. Apparatus for measuring the amount of sebum secreted by the skin of a living subject, said apparatus comprising: a casing having a side wall; a sample holder carried by said casing, means mounting said sample-holder relative to said casing for movement between an extended position and a retracted position in which it is flush with said casing; translucent means carried by said sample holder for application to the zone of skin to be studied, a calibrated spring urging said sample-holder into said extended position; a scale within the casing; reference means on said scale; and a light source within the casing for emitting a luminous flux toward said scale; so that the amount of sebum deposited on the sample-holder can be determined by observation of the reference mark of the scale through the translucent element.

2. Apparatus according to claim 1, wherein said light source comprises illuminating lamp means located between the scale and said translucent means; and electrical power source inside the casing for energizing said illuminating lamp means.

3. Apparatus according to claim 1, wherein said translucent means comprise a frosted glass plate.

4. Apparatus according to any one of claims 1 to 3, including support means mounting said scale for movement within the casing translationally relative to said translucent means, means for indicating the relative position of the scale with respect to the translucent means and comprising graduations on said wall of the casing.

5. Apparatus according to claim 2, including support means carrying said scale for movement translationally inside the casing in a direction toward and away from said translucent means, the position of said support being indicated by graduations on said wall of the casing; and wherein said support means comprises a cylinder which houses the electrical power source and which carries said illuminating lamp means, said cylinder having an end located opposite the translucent element and which is closed by said scale.

6. Apparatus according to claim 5, wherein said casing includes rectilinear slot means in the wall thereof parallel to said direction of movement of the support, said slot having parallel edges, and said support further comprises; outside said casing, a slider which travels along said rectilinear slot means, said graduations being located along one of the parallel edges of the said slot.

7. Apparatus according to any one of claims 1 to 3, wherein said scale has a series of reference marks and said translucent means is planar, and said apparatus includes means mounting said scale for movement in a plane parallel to the plane of the translucent means so as to bring each of the reference marks on the scale successively opposite the translucent means.

8. Apparatus according to claim 7, wherein said scale comprises a plate, and said casing includes means defining two apertures in the wall thereof, said apertures serving to guide the plate for movement in a plane parallel to the plane of the translucent means.

9. Apparatus according to claim 7, wherein said scale is in the form of a circular disc and including means mounting said circular disc for pivoting in a plane parallel to the plane of the translucent means, the disc having at least a sector thereof penetrating inside the casing to be disposed opposite the translucent element.

10. Apparatus according to any one of claims 1 to 3, wherein said translucent means is planar and said scale is in the form of a rotor, and means mounting said rotor pivotally inside the casing about an axis of rotation approximately parallel to said plane of the translucent means, said rotor having means defining a side wall comprising a series of reference marks which can be successively presented in alignment with the translucent means.

11. Apparatus according to claim 10, wherein said rotor side wall delimits a regular prism, and said prism has a square base and an axis which coincides with said axis of rotation of the rotor, each side face of the prism carrying a reference mark.

* * * * *